United States Patent [19]
Van Der Puy et al.

[11] Patent Number: 5,315,048
[45] Date of Patent: May 24, 1994

[54] PREPARATION OF 1,1,1,2,3-PENTAFLUOROPROPANE BY REDUCTION OF 1,2,3-TRICHLOROPENTAFLUROPROPANE

[75] Inventors: Michael Van Der Puy, Cheektowaga; David Nalewajek, West Seneca, both of N.Y.

[73] Assignee: AlliedSignal Inc., Morris Township, Morris County, N.J.

[21] Appl. No.: 130,083

[22] Filed: Sep. 30, 1993

[51] Int. Cl.$^5$ .................. C07C 17/24; C07C 19/02
[52] U.S. Cl. ........................ 570/176; 570/151
[58] Field of Search ........................... 570/151, 176

[56] References Cited

U.S. PATENT DOCUMENTS

| | | | |
|---|---|---|---|
| 2,942,036 | 6/1960 | Smith et al. | 570/176 |
| 5,091,600 | 2/1992 | Moore et al. | 570/176 |

FOREIGN PATENT DOCUMENTS

| | | | |
|---|---|---|---|
| 506525 | 9/1992 | European Pat. Off. | 570/176 |
| 539989 | 5/1993 | European Pat. Off. | 570/176 |
| 9008753 | 8/1990 | World Int. Prop. O. | 570/176 |

OTHER PUBLICATIONS

Chem. Abstr. (1991), 114, 125031q.
Chemical Abstract, (1966), 64:578e.
Chemical Abstract, (1961), 55:349f.
Chemical Abstract, (1959), 53:1102c.
Barlow, M. G. et al., "Heterocyclic Polyfluoro-compounds. Part 31. Photo chemical . . . ", J. Chem. Soc. Perkin Trans. I, (1980), pp. 2258–2267.
Henne, A. L. et al., "Perfluorinated Olefins", J. Am. Chem. Soc., (1948), 70, pp. 130–132.
Miller, W. T., Jr., et al., "Preferential Replacement Reactions of . . . ", J. Am. Chem. Soc., (1957), 79, pp. 4164–4169.

*Primary Examiner*—Alan Siegel
*Attorney, Agent, or Firm*—Karen A. Harding; Jay P. Friedenson

[57] ABSTRACT

The present invention relates to a process for the reductive dechlorination of $ClCF_2CFClCF_2Cl$ to $CF_3CHFCH_2F$ comprising the step of contacting 1,2,3-trichloropentafluoropropane and $H_2$ in the presence of a catalyst selected from the group consisting of palladium, platinum, ruthenium, rhodium, iridium and mixtures thereof supported on alumina under reaction conditions sufficient to produce a product stream containing 1,1,1,2,3-pentafluoropropane.

14 Claims, No Drawings

PREPARATION OF 1,1,1,2,3-PENTAFLUOROPROPANE BY REDUCTION OF 1,2,3-TRICHLOROPENTAFLUROPROPANE

BACKGROUND OF THE INVENTION

Hydrofluorocarbons (HFCS) are of current interest due to their potential to replace ozone depleting chlorofluorocarbons (CFCs) and hydrochlorofluorocarbons (HCFCs) which are used in a variety of applications including refrigerants, propellants, blowing agents, and solvents. The compound $CF_3CHFCH_2F$ (1,1,1,2,3-pentafluoropropane or HFC-245eb) has physical properties, including a boiling point of about 20° C., which makes it particularly attractive as a blowing agent or propellant. Ger. Omen, DE 3,903,336, 1990 (EP 381 986 A) states that fluorinated propanes may be used as a propellant or blowing agent. The use of HFC-245eb as a heat transfer agent is also mentioned in Japanese Kokai Tokyo Koho JP 02,272,086 (Chem. Abstr. 1991:114, 125031q).

HFC-245eb has been synthesized via the catalytic reduction of (1,1,1,2,3-pentafluoropropane $CF_3CF=CHF$) as reported in Chem. Abstr., 1966, 64:578e, Chem. Abstr., 1961, 55:349f, and Chem. Abstr., 1959, 53:1102c. The required olefin, $CF_3CF=CHF$, was prepared by dehydrofluorination of $CF_3CHFCHF_2$ with KOH, which in turn, was prepared by reduction of commercially available hexafluoropropene. HFC-245eb was also identified as a minor product (less than 1% yield), in the reaction of 1,2-difluoroethylene and trifluoroacetaldehyde (J. Chem. Soc. Perkin Trans. I, 1980, 2258).

However, the dehydrofluorination of $CF_3CHFCHF_2$ (HFC-236ea) is not amenable to large scale manufacture. Fluorine values are lost in the preparation of $CF_3CF=CHF$ and a considerable amount of by-product wet potassium fluoride is formed.

It is thus an object of this invention to provide a means of manufacturing 1,1,1,2,3-pentafluoropropane which avoids the above-mentioned shortcomings and which is economical and amenable to large scale, using readily available raw materials.

DESCRIPTION OF THE INVENTION

The present invention relates to a process for the reductive dechlorination of $ClCF_2CFClCF_2Cl$ to $CF_3CHFCH_2F$ comprising the step of contacting 1,2,3-trichloropentafluoropropane and $H_2$ in the presence of a catalyst selected from the group consisting of palladium, platinum, ruthenium, rhodium iridium and mixtures thereof supported on alumina under reaction conditions sufficient to produce a product stream containing 1,1,1,2,3-pentafluoropropane.

It has been unexpectedly found that while reduction of 1,2,3-trichloropentafluoropropane (CFC-215ba) with hydrogen over Pd on carbon gives primarily a mixture of $HCF_2CHFCF_2H$ and $HCF_2CHFCF_2Cl$ (U.S. application Ser. No. 08/129,879, filed on Sep. 30, 1993, reduction with hydrogen over Pd on alumina gives primarily $CF_3CHFCH_2F$.

For the reductive dechlorination of chlorinated organic compounds, platinum group metal catalysts are commonly used. Among these, palladium is generally the catalyst material of choice. For reductions of this type, the preferred physical nature of the catalyst depends somewhat on the conditions chosen for the reduction and the nature of the material to be reduced. For example, the reduction of solids or high boding liquids are frequently done in a solvent, along with an acid scavenger (NAOH or sodium acetate) using a very fine powder of Pd or Pd on carbon powder. These catalysts provide very high surface areas which are desirable for good reaction rates. For the reduction of chlorinated materials which are gases or volatile liquids, the reductions are preferably conducted in the gas phase using a flow reactor. In the present case, supported Pd catalysts are used. The support serves a number of functions. Among them are the dissipation of the heat of reduction, modification of catalyst activity, convenient catalyst recovery (the supports are generally pellets or granules of about 4-10 mesh), and primarily, to allow greater efficiency in the use of the precious metal. For the latter consideration, loadings are usually kept small, usually 0.5 to 5 weight percent.

Many support materials have been used. It is generally recognized that the support will alter the performance of the catalyst, which will be manifested in the percent conversion or extent of the reduction. It is quite unexpected, however, to observe that a change in the support leads to products with different molecular structures. However, in the reduction of 1,2,3-trichloropentafluoropropane over palladium catalysts this is exactly what happens. When activated carbon was the support, the main reaction products were the expected $HCF_2CHFCF_2H$ and $HCF_2CHFCF_2Cl$ even at temperatures up to 300° C. When the support was alumina, the main product, obtained at about 225° C., was the reduced and rearranged compound, $CF_3CHFCH_2F$.

The catalyst material is a noble metal selected from the group consisting of Pd, Pt, Rh, Ru, Ir and combinations thereof supported on aluminum oxide ($Al_2O_3$). The aluminum oxide is used in its basic form, which is also referred to as basic alumina. The catalyst material may be deposited on the support in any convenient form such as a halide or oxide of the catalyst material. Typically the desired halide or oxide salt is impregnated on the support, dried then reduced to the metal with $H_2$.

Palladium is preferred due to its relatively lower cost. The catalysts of the present invention may take any form. However, powders are not preferred because powders are small enough to be carried through the reactor or cause large pressure drops. Accordingly, the catalysts of the present invention are preferably shaped. The catalysts may be prepared in any shape, and by any technique known in the art such as extrusion or tabletting. Examples of suitable shapes include, but are not limited to large chunks, spheres and pellets.

The catalysts are available commercially and generally can be obtained having about 0.5 to about 20% by weight of the metal on the support material. More commonly, loadings of about 0.5 to about 5% weight percent are available. For example, 0.5% platinum on ⅛" alumina pellets is commercially available from Engelhard or Johnson Matthey.

The reduction may be carried out in either the liquid or the vapor phase. However, for large scale production the reaction is preferably conducted in a continuous flow system by passing vapors of $ClCF_2CFClCF_2Cl$, along with hydrogen, over one of the critically defined catalysts. The reactor is made of any corrosion resistant material, such as Inconel.

Pressure is not critical. Both subatmospheric pressures or pressures up to 100 atmospheres may be used, the latter is especially useful in batch operations. Atmospheric pressures are frequently the most convenient and are thus preferred.

Reaction temperatures ranging from about 140° to about 300° C., may be used the preferred range being from about 190° to about 2500° C.

Enough hydrogen must be used to insure the desired yields. Preferably at least 3 moles of hydrogen are fed into the reactor for every one mole of 1,2,3,-trichloropentafluoropropane. More preferably the ratio of moles of $H_2$ to moles of 1,2,3,-trichloropentafluoropropane is between about 3:1 to about 10:1.

The reactants are fed to the reactor at a rate sufficient to produce the desired HFC-245eb. Preferably contact times are from about 0.1 second to about 2 minutes and more preferably from about 3 seconds to about 20 seconds. High conversions may be achieved by recycling the product stream until the desired conversion is obtained. After separating the desired $CF_3CHFCH_2F$ from $HCF_2CHFCF_2Cl$ and other under-reduced materials that may be present, the $HCF_2CHFCF_2Cl$ may be fed into the reactor again, either alone or affixed with $ClCF_2CFClCF_2Cl$.

The HFC-245eb may be separated from the product stream via any known separation or purification method, such as distillation.

The starting material, 1,2,3-trichloropentafluoropropane was obtained commercially. Alternately, it can be prepared via the fluorination of 1,1,1,2,3,3,3-heptachlorofluoropropane in the presence of antimony fluoride (A. L. Henne and T. H. Newby (J. Am. Chem. Soc., 1948, 70, 130)) or antimony chlorofluoride (W. T. Miller and H. Fainberg (J. Am. Chem. Soc., 1957, 79, 4164)), incorporated herein by reference.

EXAMPLE 1

The hydrogenation reactor consisted of an electrically heated glass tube mounted vertically with provision for gaseous and liquid reactants to enter at the top of the reactor. Hydrogen was fed in through a gas flowmeter, while liquid reagents were fed into the reactor at a controlled rate using a syringe pump. The bottom exit of the reactor was connected to a water scrubber, a glass bulb for analyzing effluent gases during the course of the reaction, and two cold traps (−78° C.) for collecting products. The catalyst bed consisted of a mixture of 10 cc 0.5% palladium on alumina pellets (⅛ inch) and 15 cc glass helices for a total bed volume of 25 ml. Hydrogen was passed over the catalyst at 140 cc/min, while $CF_2ClCFClCF_2Cl$ (42 g total) was fed into the reactor over 4¼ hours. The temperature was increased from an initial 158° C. to a maximum of 225° C. during this period. The percentage of the expected product, $HCF_2CFHCF_2H$, in the gaseous effluent decreased as the temperature of the reaction increased. The cold traps contained 22.8 g of a mixture comprised of 7 compounds. Upon distillation, a boiling point fraction (bp 22°–25° C.) contained 86% percent of a compound, identified by GC-MS analysis as $CF_3CHFCH_2F$.

EXAMPLE 2

In a similar manner, a reactor as described above was charge with 50 cc of the same catalyst mixed with 50 cc glass helices. The temperature was kept at 155° to 169° C. while $CF_2ClCFClCF_2Cl$ was fed in at 5 ml/hour and $H_2$ at 90 cc/min. After 65 min reaction time, the product fixture consisted of 21.3% $CF_3CHFCH_2F$, 5.6% $HCF_2CHFCF_2H$, 26% $CF_2HCHFCF_2Cl$, 12.3% $CF_2ClCHFCF_2Cl$, and 20% unreacted $ClCF_2CFClCF_2Cl$.

EXAMPLE 3

Example 2 was repeated, except that the temperature was increased to 200°–243° C. and the total reaction time was increased to 2¼ h. The percent $CF_3CHFCH_2F$ in the product mixture was 56.9%.

EXAMPLE 4

Example 3 was repeated, keeping the temperature within 10° C. of 200° C., and decreasing the organic ($ClCF_2CFClCF_2Cl$) flow rate to 4 ml/h. After 8 hours, a total of 53 g was added, and 41.6 g of crude product was collected. Analysis indicated it was comprised of 5% $CF_3CH=CF_2$, 54% $CF_3CHFCH_2F$, 10% $ClCF_2CHFCF_2H$, 10% $ClCF_2CFClCF_2H$, 12% $ClCF_2CHFCF_2Cl$, and 5% $ClCF_2CFClCF_2Cl$.

Thus, Examples 2 through 4 demonstrate that $CF_2ClCFClCF_2Cl$ is readily converted to HFC-245eb over a palladium on alumina catalyst over a range of temperatures and contact times.

EXAMPLE 5

Example 4 was repeated, and the combined crude products (87 g) were used as the organic feed in this example. The conditions were as described in Example 4. The total run time was 14 hours. The % $CF_3CHFCH_2F$ in the crude product from this recycled material increased to 69%. Distillation through a 2-foot packed column afforded 29.5 g of 97% pure $CF_3CHFCH_2F$ (bp 20°–24° C.) for a yield of 55.2% based on the total amount (94.6 g) of $ClCF_2CFClCF_2Cl$ used. Thus, the yield produced may be increased by recycling the product material back through the reactor vessel.

COMPARATIVE EXAMPLE

The reactor described in Example 1 was charged with a catalyst consisting of 20 cc 1% palladium on carbon (4 to 8 mesh, purchased from Aldrich) mixed with 10 cc glass helices. Hydrogen flow rate was 140 cc/min. The reactor temperature was 255°–2650° C. during most of the 4.5 hour run time. A total of 46.8 g $ClCF_2CFClCF_2Cl$ was charged and 25.1 g product was collected in the cold traps. Gas chromatographic analysis of this material indicated <3% low boiling components, 39% $HCF_2CHFCF_2H$, 51% $HCF_2CHFCF_2Cl$ and 7% $C_3HCl_2F_5$.

Thus, it is clear that when alumina is the support the desired HFC-245eb is produced, and when carbon is the support the expected HFC-245ca is produced.

We claim:

1. A process comprising the step of contacting 1,2,3-trichloropentafluoropropane and $H_2$ in the presence of a catalyst selected from the group consisting of palladium, platinum, ruthenium, rhodium, iridium and mixtures thereof supported on alumina under reaction conditions sufficient to produce 1,1,1,2,3-pentafluoropropane.

2. The process of claim 1 wherein said contacting step is conducted in the vapor phase.

3. The process of claim 1 wherein said catalyst is palladium.

4. The process of claim 3 wherein said conditions include temperatures between about 140° C. to about 300° C.

5. The process of claim 4 wherein said conditions include temperatures between about 190° C. to about 250° C.

6. The process of claim 4 wherein said conditions include contact times from about 0.1 second to about 2 minutes.

7. The process of claim 6 wherein said contacts times range from about 3 to about 20 seconds.

8. The process of claim 1 additionally comprising the step of recycling at least a part of the product strewn containing the 1,1,1,2,3-pentafluoropropane over the catalyst to produce more 1,1,1,2,3-pentafluoropropane.

9. The process of claim 1 wherein said catalyst is platinum.

10. The process of claim 9 wherein said conditions include temperatures between about 140° C. to about 300° C.

11. The process of claim 10 wherein said conditions include temperatures between about 190° C. to about 250° C.

12. The process of claim 10 wherein said conditions include contact times from about 0.1 second to about 2 minutes.

13. The process of claim 12 wherein said contacts times range from about 3 to about 20 seconds.

14. The process of claim 13 additionally comprising the step of recycling at least a part of the product stream containing the 1,1,1,2,3-pentafluoropropane over the catalyst to produce more 1,1,1,2,3-pentafluoropropane.

* * * * *